United States Patent
Hall et al.

(10) Patent No.: US 6,193,665 B1
(45) Date of Patent: Feb. 27, 2001

(54) DOPPLER ANGLE UNFOLDING IN ULTRASOUND COLOR FLOW AND DOPPLER

(75) Inventors: Anne Lindsay Hall, New Berlin; Fang Dong, Middleton, both of WI (US)

(73) Assignee: General Electric Company, Milwaukee, WI (US)

( * ) Notice: Subject to any disclaimer, the term of this patent is extended or adjusted under 35 U.S.C. 154(b) by 0 days.

(21) Appl. No.: 09/224,652

(22) Filed: Dec. 31, 1998

(51) Int. Cl.[7] ........................................... A61B 8/06
(52) U.S. Cl. ............................................... 600/455
(58) Field of Search .................. 600/441, 453–457

(56) References Cited

U.S. PATENT DOCUMENTS

| | | | |
|---|---|---|---|
| 4,622,978 | * 11/1986 | Matsuo et al. | 600/457 |
| 5,038,788 | * 8/1991 | Satake | 600/455 |
| 5,349,524 | 9/1994 | Daft et al. | |
| 5,441,052 | * 8/1995 | Miyajima | 600/455 |
| 5,454,372 | 10/1995 | Banjanin et al. | |
| 5,522,393 | * 6/1996 | Phillips et al. | 600/455 |
| 5,538,004 | * 7/1996 | Bamber | 600/443 |
| 5,555,886 | * 9/1996 | Weng et al. | 600/456 |
| 5,910,119 | * 6/1999 | Lin | 600/455 |
| 5,997,480 | * 12/1999 | Sumanaweera et al. | 600/456 |

FOREIGN PATENT DOCUMENTS

WO 97/32777   9/1997  (WO).

OTHER PUBLICATIONS

LEAVITT et al. *A Scan Coversion Algorithm for Displaying Ultrasound Images*, Hewlett–Packard Journal, Oct. 1983, vol. 34, No. 10, 1266 Amstelveen, Nederland.

OVERBECK et al. *Vector Doppler: Accurate Mesasurement of Blood Velocity In Two Dimensions*, Ultrasound in Med. & Biol., 1992, Vol, 18, No. 1, pp. 19–31, U.S.A.

CHEN et al. *Symmetric Phase–Only Matched Fitlering of Fourier–Mellin Transforms for Image Registration and Recognition*, 8180 IEEE Transactions on Pattern Analysis and Machine Intelligence, (1994) Dec., No. 12, U.S.A.

* cited by examiner

Primary Examiner—Francis J. Jaworski
(74) Attorney, Agent, or Firm—McAndrews Held and Malloy; Christian G. Cabou; Phyllis Y. Price

(57) ABSTRACT

An ultrasonic imaging system for displaying velocity of fluid includes a receiver which demodulates ultrasonic echo signals received by a transducer array from two different positions. The resulting data is organized into frames of data from the two different positions. The data is used to calculate the angle of rotation between the frames. The fluid flow velocity then is calculated from the frames of data and the angle of rotation.

16 Claims, 5 Drawing Sheets

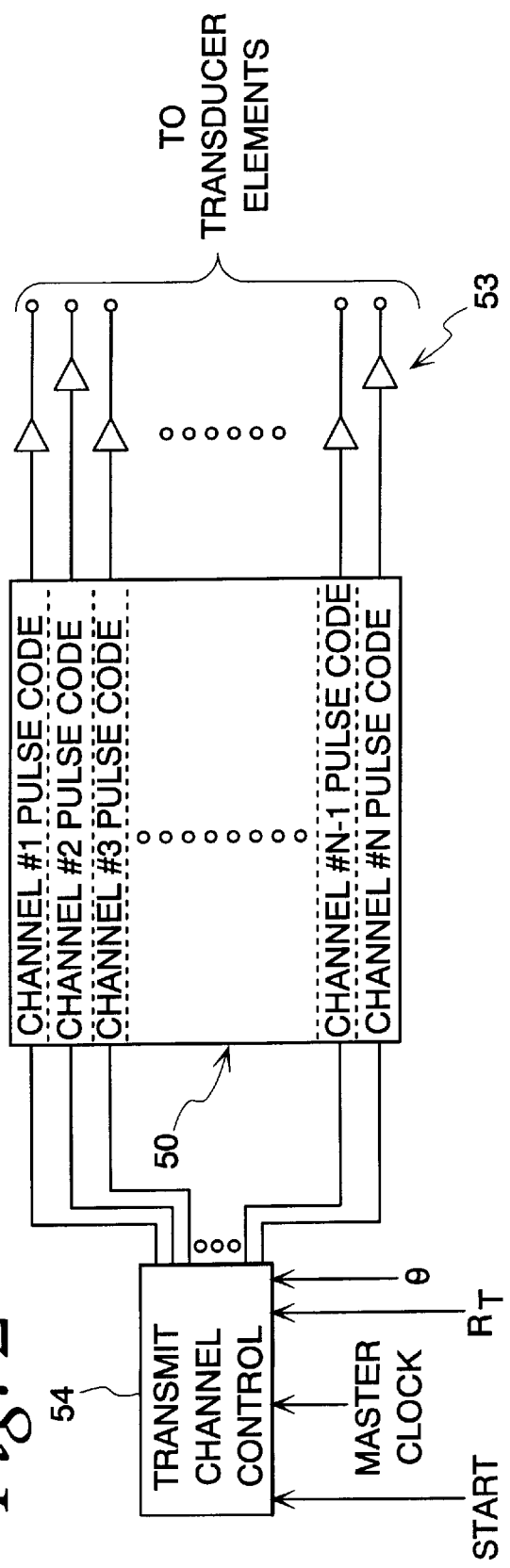
*Fig. 2*
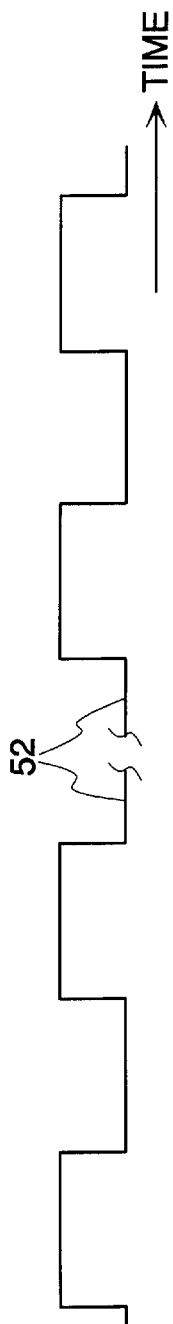
*Fig. 2A*
*Fig. 2B*

DOPPLER ANGLE UNFOLDING IN ULTRASOUND COLOR FLOW AND DOPPLER

BACKGROUND OF THE INVENTION

This invention relates to acoustical Doppler velocity estimations and, more specifically, relates to the calculation of body fluid velocity, such as blood velocity and the like, based on the Doppler shift of ultrasonic signals.

Color flow and Doppler imaging in current ultrasound systems are both affected by the same limitation. If a Doppler style processing, such as a Fourier transform for Doppler or an autocorrelation for color flow (or exclusively down-range processing, such as a time domain cross correlation algorithm) are used to measure either blood flow or tissue motion, only the velocity component along the line of the ultrasound beam direction is measured, and any orthogonal component is not usually calculated. Various schemes have been proposed and even implemented to compensate for this problem. In Doppler, the user is typically given the opportunity to position a cursor indicating the direction of blood flow, so that the true velocity vector then can be adjusted by the cosine of the Doppler angle. In color flow, various schemes, including triangulation and lateral cross correlation, have been studied and published in the literature. However, none of the known systems effectively calculates the true velocity of blood flow in a manner which eliminates operator errors. This invention solves that problem.

BRIEF SUMMARY OF THE INVENTION

The present invention is useful in an ultrasound imaging system for calculating the velocity of fluid flow, such as blood flow, in at least a portion of a subject being studied. As used in the specification and claims, fluid flow includes blood flow, tissue flow and flow of contrast agents used in diagnosis, including those which result in bubbles in the blood stream. Preferably, ultrasound waves are transmitted from a first position toward a portion of the subject by a conventional ultrasound transducer. First reflected ultrasound waves traveling in a first direction are received from the portion of the subject in response to the transmitting of the ultrasound waves from the first position, preferably by an ultrasound transducer. Ultrasound waves are transmitted from a second position toward the portion of the subject. Second reflected ultrasound waves traveling in a second direction are received from the portion of the subject in response to the transmitting of the ultrasound waves from the second position. A first signal is generated having a first value related to the velocity component of the fluid flow in at least the portion of the subject in response to the first reflected ultrasound waves, preferably by a Doppler unit. A second signal is generated having a second value related to the velocity component of the fluid flow in at least the portion of the subject in response to the second reflected ultrasound waves, preferably by the Doppler unit. First scan data is generated and stored in response to the first ultrasound waves received from the portion of the subject in response to the transmitting of the ultrasound waves from the first position, preferably by a B-mode or color ultrasound scanner and memory. Second scan data is generated and stored responsive to the second ultrasound waves received from the portion of the subject in response to the transmitting of the ultrasound waves from the second position. The angle of rotation between the first position and the second position is calculated in response to the first and second scan data, preferably by a logic unit, such as a processor. The velocity of the fluid flow in at least the portion of the subject is estimated based on the angle of rotation and the first and second values of the first and second signals.

The advantage of this technique is that a more accurate estimate of the fluid flow/tissue velocity is obtained by the system, thus aiding the diagnosis of the disease state being studied. With additional information, such as vessel cross-sectional area, estimates of quantitative fluid flow, such as blood flow, can potentially be obtained.

BRIEF DESCRIPTION OF THE DRAWINGS

FIG. 2 is a schematic block diagram of a transmitter which forms part of the system of FIG. 1;

FIGS. 2A and 2B are graphical representations of the signal in any of the channels of transmitter 50 of FIG. 2;

DETAILED DESCRIPTION OF THE INVENTION

Figure 1:
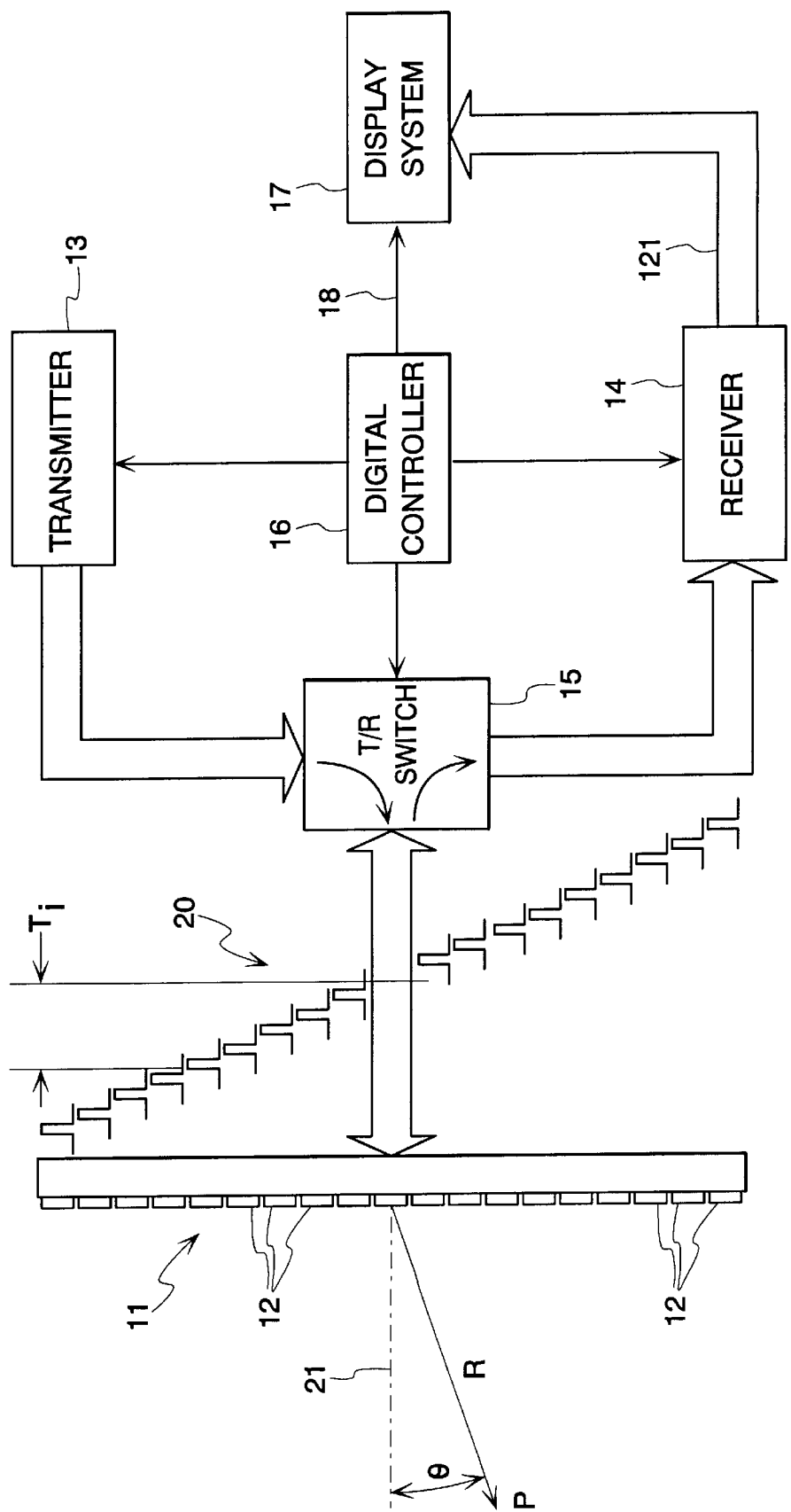
FIG. 1 is a schematic block diagram of an ultrasonic imaging system employing a preferred embodiment of the present invention.

Referring to FIG. 1, a vibratory energy imaging system includes a transducer array 11 comprised of a plurality of separately driven elements 12 which each produce a burst of ultrasonic energy when energized by a pulsed waveform produced by a transmitter 13. The ultrasonic energy reflected back to transducer array 11 from the subject under study is converted to an electrical signal by each transducer element 12 and applied separately to a receiver 14 through a set of transmit/receive (T/R) switches 15. Transmitter 13, receiver 14 and switches 15 are operated under control of a digital controller 16 responsive to commands by a human operator. A complete scan is performed by acquiring a series of echoes in which switches 15 are sent to their transmit position, transmitter 13 is gated on momentarily to energize each transducer element 12, switches 15 are then set to their receive position, and the subsequent echo signals produced by each transducer element 12 are applied to receiver 14. The separate echo signals from each transducer element 12 are combined in receiver 14 to produce a single echo signal which is employed to produce a line in an image on a display system 17.

Transmitter 13 drives transducer array 11 such that the vibrational energy produced, e.g., ultrasonic energy, is directed, or steered, in a beam. A B-scan can therefore be performed by moving this beam through a set of angles from point-to-point rather than physically moving transducer array 11. To accomplish this, transmitter 13 imparts a time delay ($T_i$) to the respective pulsed waveforms 20 that are applied to successive transducer elements 12. If the time delay is zero ($T_i$=0), all the transducer elements 12 are energized simultaneously and the resulting ultrasonic wave is directed along an axis 21 normal to the transducer face. As the time delay ($T_i$) is increased as illustrated in FIG. 1, the ultrasonic wave is directed downward from central axis 21 by an angle θ. The wave is focused at a range $R_T$, thereby forming a beam. The relationship between the time delay $T_i$ applied to each $i^{th}$ signal from one end of the transducer array (i=1) to the other end (i=n) is given by the following relationship:

$$T_i = R_T/c - \sqrt{(R_{T/c})^2 + (x/c)^2 - 2xR_T \sin\theta/c^2} \quad (1)$$

where:
- x=distance of center of transducer element 12 from center of transducer array;
- θ=transmit beam angle,
- c=velocity of sound in the object under study, and
- $R_T$=range at which transmit beam is focused.

The time delays $T_i$ in equation (1) have the effect of steering the beam in the desired angle θ, and causing it to be focused at a fixed range $R_T$. A sector scan is performed by progressively changing the time delays $T_i$ in successive excitations. The angle θ is thus changed in increments to steer the transmitted beam in a succession of directions. When the direction of the beam is above central axis 21, the timing of pulses 20 is reversed, but the formula of equation (1) still applies.

Referring still to FIG. 1, the echo signals produced by each burst of ultrasonic energy emanate from reflecting objects located at successive positions (R) along the ultrasonic beam. These are sensed separately by each segment 12 of transducer array 11 and a sample of the magnitude of the echo signal at a particular point in time represents the amount of reflection occurring at a specific range (R). Due to the differences in the propagation paths between a reflecting point P and each transducer element 12, however, these echo signals will not occur simultaneously and their amplitudes will not be equal. The function of receiver 14 to amplify and demodulate these separate echo signals, impart the proper time delays to each and sum them together to provide a single echo signal which accurately indicates the total ultrasonic energy reflected from point P located at R along the ultrasonic beam oriented at the angle θ.

To simultaneously sum the electrical signals produced by the echoes from each transducer element 12, time delays are introduced in to each separate transducer element channel of receiver 14. The beam time delays for reception are the same delays ($T_i$) as the transmission delays described above. However, in order to dynamically focus, the time delay of each receiver channel is continuously changing during reception of the echo to provide dynamic focusing of the received beam at the range R from which the echo signal emanates. The exact equation for the time delay $T_d$ imposed on the signal received by each transducer element is as follows:

$$T_d = t/2 - \sqrt{(t/2)^2 + (x/c)^2 - (xt/c)\sin(\theta)} \quad (2)$$

where:
- t=elapsed time after transmission of sound from center of transducer array (i.e., START),
- c=velocity of sound in the object under study,
- θ=beam angle, and
- x=distance of center of element from center of transducer array.

Under direction of digital controller 16, receiver 14 provides delays during the scan such that steering of receiver 14 tracks with the direction θ of the beam steered by transmitter 13 and it samples the echo signals at a succession of ranges R and provides the proper delays to dynamically focus at points P along the beam. Thus, each emission of an ultrasonic pulse waveform results in the acquisition of a series of data points which represent the amount of reflected sound from a corresponding series of points P located along the ultrasonic beam.

Display system 17 receives the series of data points produced by receiver 14 and converts the data to the form and geometry required to produce desired image. For example, if an A-scan is desired, the magnitude of the series of data points is merely graphed as a function of time. If a B-scan is desired, each data point in the series is used to control brightness of a pixel in the image, and a scan comprised of a series of measurements at successive steering angles (θ) is performed to provide the data necessary for display.

Referring to FIG. 2 in conjunction with FIG. 1, transmitter 13 includes a set of channel pulse code memories indicated collectively as memories 50. In the preferred embodiment there are 128 separate transducer elements 12, and therefore, there are 128 separate channel pulse code memories 50. Each pulse code memory 50 is typically an n-bit by 512-bit memory which stores a bit pattern 51 that determines the frequency of the ultrasonic pulse 52 to be produced. In the preferred embodiment, this bit pattern is read out of each pulse code memory 50 by a 40 MHz master clock and applied to a driver 53 which amplifies the signal to a power level suitable for driving transducer 11. In the example shown in FIG. 2a, the bit pattern is a sequence of four "1" bits alternated with four "−1" bits to produce a 5 MHz ultrasonic pulse 52; however, other carrier frequencies ($F_0$) may be employed in the preferred embodiment, such as 2.5, 3.75, 6.25, 7.5, 8.75 and 10 MHz. Transducer elements 12 to which these ultrasonic pulses 52 are applied respond by producing ultrasonic energy. If all 512 bits are used, a pulse of bandwidth as narrow as 40 kHz centered on the carrier frequency (i.e. 5 MHz in the example) will be emitted.

As indicated above, to steer the transmitted beam of the ultrasonic energy in the desired direction (θ), pulses 52 for each of the n channels, such as shown in FIG. 2B, must be delayed by the proper amount. These delays are provided by a transmit control 54 which receives four control signals (START,MASTER CLOCK, $R_T$ and θ) from digital controller 16 (FIG. 1). Using the input control signal θ, the fixed transmit focus $R_T$, and the above equation (1), transmit control 54 calculates the delay increment $T_i$ required between successive transmit channels. When the START control signal is received, transmit control 54 gates on e of four possible phases of the 40 MHz MASTER CLOCK signal through to the first transmit channel 50. At each successive delay time interval ($T_i$) thereafter, the 40 MHz MASTER CLOCK signal is gated through to the next channel pulse code memory 50 until all n=128 channels are producing their ultrasonic pulses 52. Each transmit channel 50 is reset after its entire bit pattern 51 has been transmitted and transmitter 13 then waits for the next θ and next START control signals from digital controller 16. As indicated above, in the preferred embodiment of the invention a complete B-scan is comprised of 128 ultrasonic pulses steered in Δθ increments which may vary as a function of θ through a 90° sector centered about central axis 21 (FIG. 1) of the transducer 11.

For a detailed description of the transmitter 13, reference is made to commonly assigned U.S. Pat. No. 5,014,712 issued May 14, 1991 and entitled "Coded Excitation For Transmission Dynamic Focusing of Vibratory Energy Beam" incorporated herein by reference.

Figure 3:
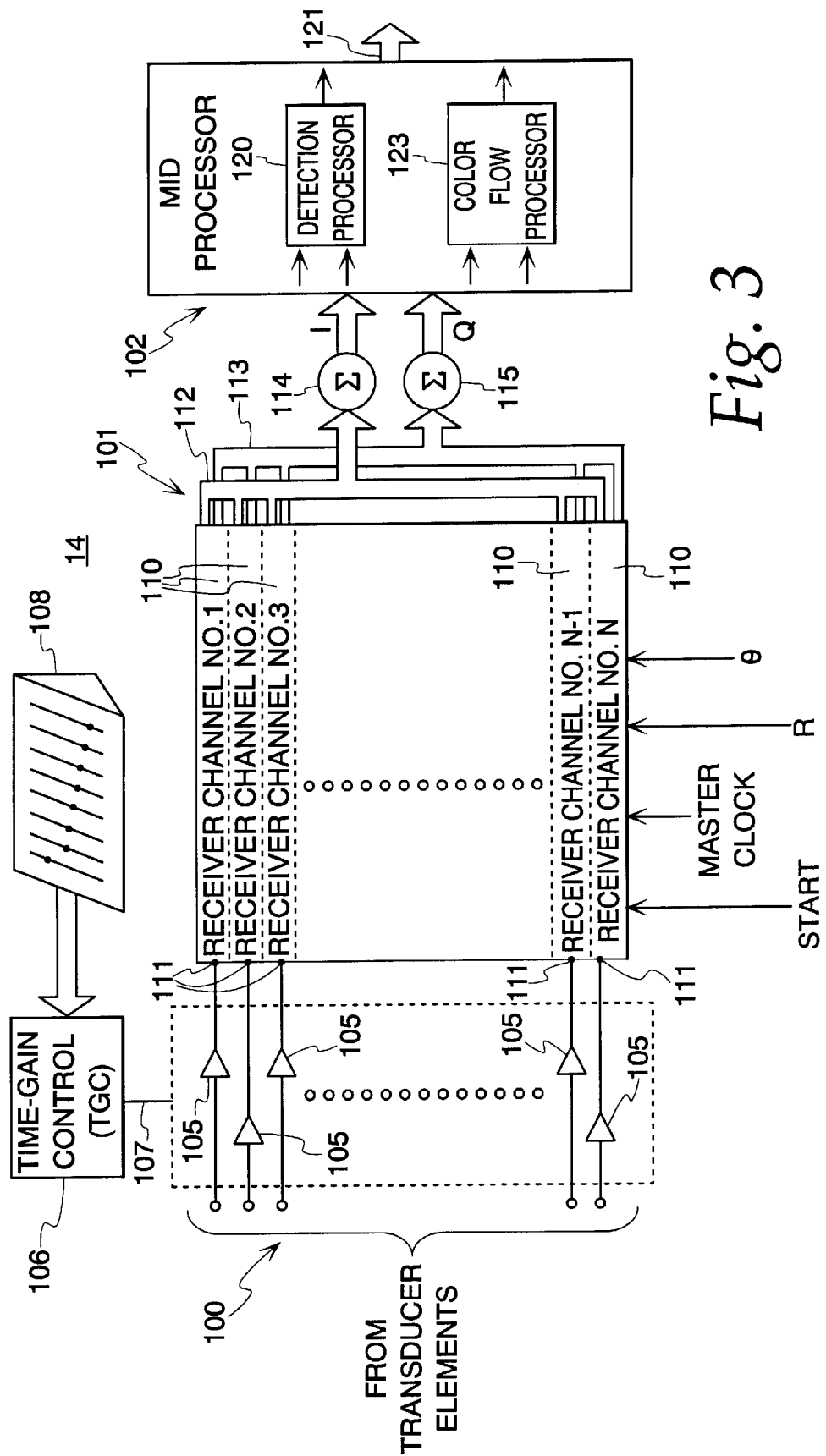
FIG. 3 is a schematic block diagram of a receiver which forms part of the system of FIG. 1.

Referring particularly to FIG. 3, receiver 14 is comprised of these sections: a time-gain control section 100, a receive beam forming section 101, and a mid processor 102. Time-gain control (or TGC) section 100 includes an amplifier 105 for each of the n=128 receiver channels and a time-gain control circuit 106. The input of each amplifier 105 is connected to a respective e o of transducer elements 12 to receive and amplify the echo signal which it receives. The amount of amplification provided by amplifiers 105 is controlled through a control line 107 that is driven by TGC circuit 106. As is well known in the art, as the range of the echo signal increases, its amplitude is diminished. As a result, unless the echo signal emanating from more distant reflectors is amplified more than the echo signal from nearby reflectors, the brightness of the image diminishes rapidly as a function of range (R). The amplification is provided in part by a base gain curve which generally is a linear ramp. The base gain curve is adjusted by the operator who manually sets eight (typically) TGC linear potentiometers 108 to values which provide a relatively uniform brightness over the entire range of the section scan. The time interval over which the echo signal is acquired determines the range from which it emanates, and this time interval is divided into eight segments by TGC circuit 106. The settings of the eight potentiometers are employed to set the gains of amplifiers 105 during each of the eight respective time intervals so that the echo signal is amplified in ever increasing amounts over the echo signal acquisition time interval.

The receive beam forming section 101 of receiver 14 includes 128 separate receiver channels 110. As will be explained in more detail below, each receiver channel 110 receives the analog echo signal from one of amplifiers 105 at an input 111, and it produces a stream of digitized output values on an I bus 112 and a Q bus 113. Each of these I and Q values represents a demodulated sample of the echo signal envelope at a specific range (R). These samples have been delayed such that when they are summed at summing points 114 and 115 with the I and Q samples from each of the other receiver channels 110, they indicate the magnitude and phase of the echo signal reflected from a point P located at range R on the steered beam (θ). In the preferred embodiment, each echo signal is sampled at 150 micrometer increments over the entire range of the scan line (typically 40 to 200 millimeters).

For a more detailed description of receiver 14, reference is made to commonly assigned U.S. Pat. No. 4,983,970, issued Jan. 8, 1991 and entitled "Method And Apparatus for Digital Phase Array Imaging", which is incorporated herein by reference.

Referring still to FIG. 3, mid processor section 102 receives the beam samples from summing points 114 and 115. The I and Q values of each beam sample are 20-bit digital numbers representing the in-phase and quadrature components of the magnitude of the reflected sound from a point (R, θ). Mid processor 102 can perform a variety of calculations on these beam samples, where choice is determined by the type of image to be reconstructed. For example, if a conventional magnitude image is to be produced, a detection logic unit 120 (FIG. 3) is implemented in which a digital magnitude M is calculated from each receive beam sample and produced at output 121 along with the R, θ coordinates of the reflection point, according to $$M=\sqrt{I^2+Q^2} \qquad (3)$$

Detection logic unit 120 may also implement correction methods such as that disclosed in commonly assigned U.S. Pat. No. 4,835,689, issued May 30, 1989 and entitled "Adaptive Coherent Energy Beam Formation Using Phase Conjungation". Such correction methods examine the received beam samples and calculate corrective values that can be used in subsequent measurements by transmitter 13 and receiver 14 to improve beam focusing and steering. Such corrections are necessary, for example, to account for the nonhomogeneity of the media through which the sound from each transducer element travels during a scan.

Processor 102 also includes a color flow processor 123 which may be constructed in the manner shown in FIG. 6 of U.S. Pat. No. 5,349,524 (Daft et al.) which is incorporated by reference and which is assigned to the same assignee as the present application.

Processor 102 may be implemented by various forms of logic units, including microprocessors, micro sequencers, microcontrollers, digital signal processors and hard-wired calculators.

Figure 4:
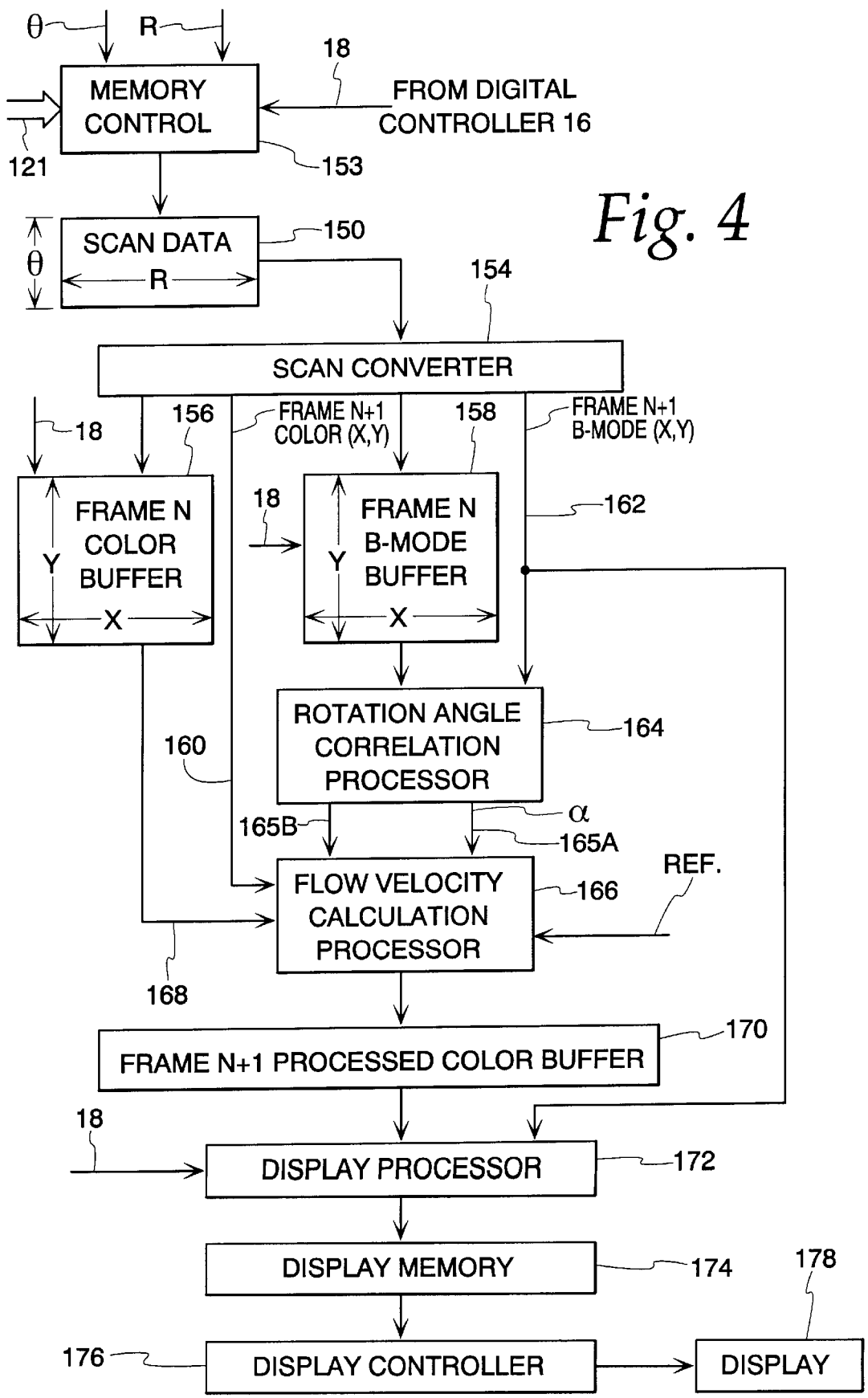
FIG. 4 is a schematic block diagram of velocity calculating circuits of the display system which forms part of the system of FIG. 1.

Referring particularly to FIGS. 1 and 4, receiver 14 generates a stream of 8-bit digital numbers at its output 121, which is applied to the input of display system 17. Each output includes an 8-bit tissue magnitude and a 12-bit flow value. These "scan data" are stored in a memory 150 as an array, with the rows of scan data array 150 corresponding with the respective beam angles (θ) that are acquired, and the columns of scan data 150 corresponding with the respective ranges R at which samples are acquired along each beam. The R and θ control signals 151 and 152 from receiver 14 indicate where each input value is to be stored in array 150, and a memory control circuit 153 writes that value to the proper memory location in array 150. The scan can be continuously repeated and the flow of values from receiver 14 will continuously update scan data array 150.

Referring still to FIG. 4, the scan data in array 150 are read by a digital scan converter 154 and converter to a form producing the desired image. If a conventional B-scan image is being produced, for example, the tissue magnitude and flow values M(R,θ) stored in the scan data array 150 are converted to values M(x,y) which indicate gray shade (for tissues) and color (for flow) at pixel locations (x,y) in the image. Such a polar coordinate to Cartesian coordinate conversion of the ultrasonic image data is described for example, in an article by Steven C. Leavitt et. al. in Hewlett-Packard Journal, October 1983, pp. 30–33, entitled "A Scan Conversion Algorithm for Displaying Ultrasonic Images."

Regardless of the particular conversion made by digital scan converter 154, the resulting image data are written to memories 156 and 158 which store two-dimensional rectangular coordinate arrays of converted scan data.

Memory 156 stores frame N color data based on color scanning performed by receiver 14, whereas a bus 160 transmits frame N+1 color data from scan converter 154 to a flow velocity calculation processor 166. Flow velocity calculation processor 166 may be constructed and operated in accordance with the information provided in a paper entitled "Vector Doppler: Accurate Measurement of Blood Velocity in Two Dimensions." by Overbeck et. al., published in *Ultrasound in Medicine and Biology,* Volume 18, No. 1, pp 19–31 (1992) which is in corporated by reference.

Memory 158 stores frame N B-mode scan data from scan converter 154, whereas a bus 162 transmits frame N+1 B-mode data from scan converter 154 to a rotation angle correlation processor 164 and to a display processor 172.

Processor 164 may be constructed and operated in accordance with the information provided in a paper entitled "Symmetric Phase-only Matched Filtering of Fourier-Mellin Transforms for Image Registration and Recognition," by Chen et al., published in Volume 16, No. 12 of the IEEE Transactions on Pattern Analysis and Machine Intelligence, pp. 1156–1168, (December 1994) which is incorporated by reference. The purpose of this processor is to calculate the relative angle between B-mode frame N and frame N+1. This relative angle will be used for the flow velocity calculation.

Using the input from processor 164, processor 166 estimates the true velocity of blood flow based on the frame N and frame N+1 color data transmitted on buses 160 and 168. The resulting data is stored in a frame N+1 processed color buffer 170.

Figure 5:
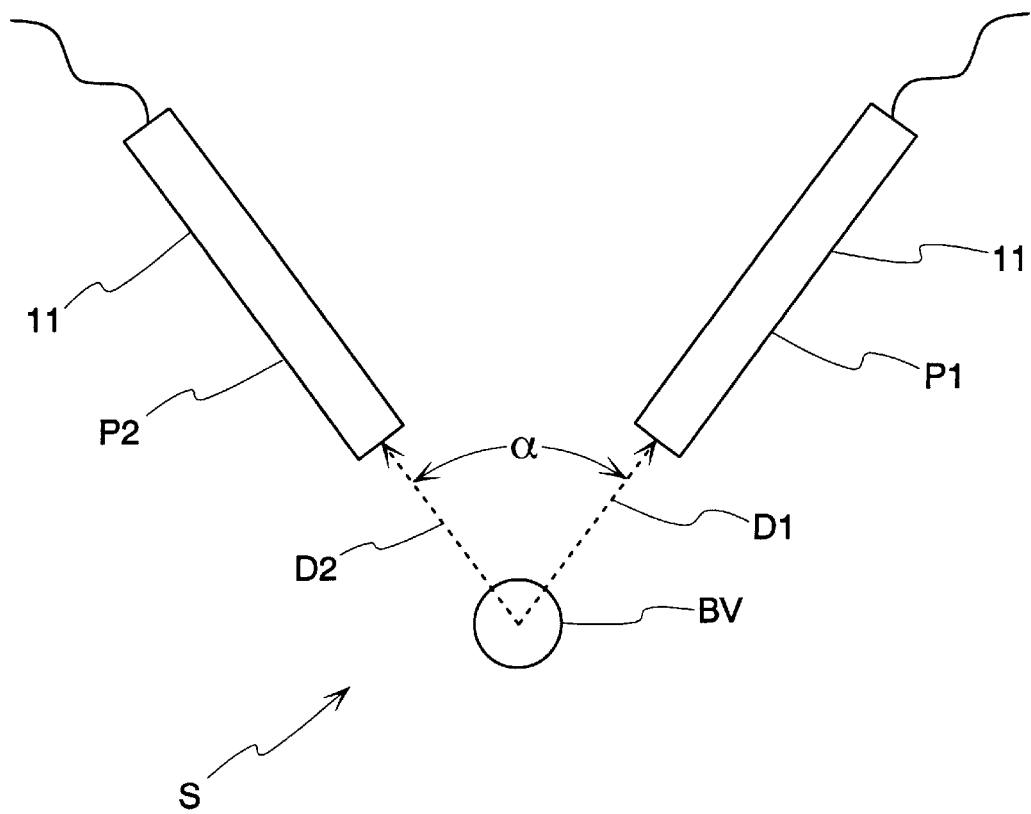
FIG. 5 illustrates the positioning of the transducer of FIG. 1 during use of the preferred embodiment.

Referring to FIG. 5, transducer 11 is used for calculating the velocity of blood flow in at least a portion of a blood vessel BV of a subject under study S, such as a human patient. Transducer 11 is placed into a position P1 from which it transmits ultrasound waves towards blood vessels BV and receives reflected ultrasound waves traveling along a directional vector D1 from blood vessel BV. The region of blood vessel BV is scanned in position P1 by transmitter 13 and receiver 14 so that color data and B-mode data is acquired from the reflected ultrasound waves received in position P1 and is stored in frame N color buffer 156 and frame N B-mode buffer 158 (FIG. 4).

Transducer 11 is then rotated to position P2, and the process is repeated. Ultrasound waves are transmitted toward blood vessel BV and reflected ultrasound waves are received from blood vessel BV traveling along a directional vector D2. The region of blood vessel BV is scanned in position P2 by transmitter 13 and receiver 14 so that a frame N+1 of B-mode data is transmitted from scan converter 154 on bus 162, and a frame N+1 of color data is transmitted from scan converter 154 on bus 160. Thus, the data in frames N stored in buffers 156 and 158 are obtained while transducer 11 is in position P1, whereas the data in frames N+1 transmitted on busses 160 and 162 are obtained while transducer 11 is in position P2 as shown in FIG. 5. The rotation of the transducer can be done by simple operator hand motion since the relative angle between position P1 and P2 is calculated for each B-mode frame N and N+1.

Based on the data from the B-mode scan frame N and B-mode scan frame N+1, processor 164 uses a registration algorithm such as a described in the Chen et al. article to calculate the angle of rotation between the B-mode frames which represents the angle between positions P1 and P2. As shown in FIG. 5, this is the angle α. Digital values representing the angle α are transmitted over a bus 165A (FIG. 4).

Based on the registration of B-mode frames N and N+1, information about registration of color frames N and N+1 is transmitted over a bus 165B. The corresponding data in color and B-mode frames are maintained in registration by storing the data in corresponding memory locations. As a result, processor 166 performs calculations on data pairs resulting from ultrasound scanning of the same volume of space inside a subject of study (i.e., from the same portion of blood vessel BV (FIG. 5)).

Based on the angle α and the registration data calculated by processor 164, processor 166 resolves orthogonal velocity vector components to calculate the velocity of the blood flowing in blood vessel BV (FIG. 5) based on the following equations:

$$f_1 = \frac{2Fo}{c} V \cos \theta \quad (4)$$

$$f_2 = \frac{2Fo}{c} V \cos (\theta + \alpha) \quad (5)$$

Where $f_1$ is the Doppler frequency received by the transducer 11 at a position P1, $f_2$ is the Doppler frequency received by the transducer at position P2, $F_0$ is the transmitted frequency, V is the magnitude of the velocity of the blood traveling at an angle θ relative to P1, c is the speed of sound in blood and α is the angle calculated by the rotation angle correlation processor. Since there are two equations and two unknowns (V and θ), the equations can be solved explicitly for the unknowns.

Based on the foregoing equations, processor 166 calculates the true velocity of the blood flowing in blood vessels BV (FIG. 5) represented by the frame N and frame N+1 of color data. The resulting velocity data is stored in the frame N+1 process color buffer 170.

Digital scan converter 154 can continuously update the values with fresh data while display processor 172 reads the updated data from memory 170 and bus 162. Display processor 172 is responsive to operator commands received from a control panel to perform conventional image processing functions on the color scan data in memory 170 and the B-mode data received on bus 162. For example, the range of brightness levels indicated by the converted scan data in memory 170 may far exceed the brightness range of display device 178. Indeed, the brightness resolution of the converted scan data in memory 170 may far exceed the brightness resolution of the human eye, and manually operable controls are typically provided which enable the operator to select a window of brightness values over which maximum image contrast is achieved. The display processor reads the converted scan data from memory 170, provides the desired image enhancement, and writes the enhanced values to a display memory 174. The display processor 172 also combines B-mode data from frame N+1 on bus 162 with color data from buffer 170 in a well known manner. Typically, color data is used in only a small portion of display 178.

Display memory 174 is controlled by a display controller circuit 176, and the values in memory 174 are mapped to control brightness and color of the corresponding pixels in display 178. Display controller 176 is a commercially available integrated circuit which is designed to operate the particular type of display 178 used. For example, display 178 may be a CRT (cathode ray tube), in which case display controller 178 is a CRT controller chip which provided the required sync pulses for the horizontal and vertical sweeps circuits and maps the display data to the CRT at the appropriate time during the sweep.

It should be apparent to those skilled in the art that display system 17 may take one of many forms depending on the capability and flexibility of a particular ultrasound system. In the preferred embodiment described above, programmed microprocessors are employed to implement the digital scan converter and display processor functions, and the resulting display system is, therefore, very flexible and powerful.

While only certain preferred features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. In an ultrasound imaging system for calculating the velocity of fluid flow in at least a portion of a subject being studied, improved apparatus comprising in combination:
   a transducer assembly operable in a first position for transmitting ultrasound waves toward the portion of the subject and receiving first reflected ultrasound waves from the portion and operable in a second position for transmitting ultrasound waves toward the portion of the subject and receiving second reflected ultrasound waves traveling from the portion, the angle between the first position and the second position being unknown;

an ultrasound receiver unit connected to generate a first signal having a first value related to a velocity component of the fluid flow in at least the portion of the subject in response to the first reflected ultrasound waves and connected to generate a second signal having a second value related to a velocity component of the fluid flow in at least the portion of the subject in response to the second reflected ultrasound waves;

a memory for storing first scan data responsive to the first ultrasound waves received from the portion of the subject at the first position and second scan data responsive to the second ultrasound waves received from the portion of the subject at the second position; and a logic unit connected to calculate the angle of rotation of the transducer assembly between the first position and the second position in response to the first and second scan data and also connected to estimate the velocity of the fluid flow in at least the portion of the subject based on the angle of rotation and the first and second values of the first and second signals.

2. Apparatus, as claimed in claim 1, wherein the transducer assembly continuously transmits and receives ultrasound waves.

3. Apparatus, as claimed in claim 1, wherein the transducer assembly transmits pulses of ultrasound waves.

4. Apparatus, as claimed in claim 1, wherein the logic unit calculates the angle of rotation by using a frequency domain registration algorithm.

5. Apparatus, as claimed in claim 1, wherein the first scan data comprises at least a first frame of scan data and the second scan data comprises at least a second frame of scan data.

6. Apparatus, as claimed in claim 5, and further comprising a scan converter connected to convert the first frame of data and second frame of data based on rectangular coordinates.

7. Apparatus, as claimed in claim 1, wherein the first and second scan data comprises B-mode scan data.

8. Apparatus, as claimed in claim 7, wherein the first and second scan data further comprises color scan data.

9. In an ultrasound imaging system for calculating the velocity of fluid flow in at least a portion of a subject being studied, an improved method comprising the steps of:

transmitting ultrasound waves from a first position toward a portion of the subject;

receiving first reflected ultrasound waves from the portion of the subject in response to the transmitting of the ultrasound waves from the first position;

transmitting ultrasound waves from a second position toward the portion of the subject;

receiving second reflected ultrasound waves from the portion of the subject in response to the transmitting of the ultrasound waves from the second position, the angle between the first position and the second position being known;

generating a first signal having a first value related to the velocity component of the fluid flow in at least the portion of the subject in response to the first reflected ultrasound waves;

generating a second signal having a second value related to the velocity component of the fluid flow in at least the portion of the subject in response to the second reflected ultrasound waves;

generating and storing first scan data responsive to the first ultrasound waves received from the portion of the subject in response to the transmitting of the ultrasound waves from the first position;

generating and storing second scan data responsive to the second ultrasound waves received from the portion of the subject in response to the transmitting of the ultrasound waves from the second position;

calculating the angle of rotation between the first position and the second position in response to the first and second scan data; and estimating the velocity of the fluid flow in at least the portion of the subject based on the angle of rotation and the first and second values of the first and second signals.

10. A method, as claimed in claim 9, wherein the steps of transmitting each comprise the steps of continuously transmitting ultrasound waves.

11. A method, as claimed in claim 9, wherein the steps of transmitting each comprise the step of transmitting pulses of ultrasound waves.

12. A method, as claimed in claim 9, wherein the step of calculating the angle of rotation comprises the step of using a frequency domain registration algorithm.

13. A method, as claimed in claim 9, wherein the first scan data comprises at least a first frame of scan data and the second scan data comprises at least a second frame of scan data.

14. A method, as claimed in claim 13, wherein the first frame of data and second frame of data are based on rectangular coordinates.

15. A method, as claimed in claim 9, wherein the steps of generating and storing first and second scan data comprise the steps of performing a B-mode scan.

16. A method, as claimed in claim 15, wherein the steps of generating and storing first and second scan data comprise the steps of performing a color scan.

* * * * *